United States Patent [19]

Köhler et al.

[11] Patent Number: 5,656,684

[45] Date of Patent: Aug. 12, 1997

[54] SILANES CONTAINING OXALAMIDE FUNCTIONAL GROUPS AND THEIR USE AS PLASTICS ADDITIVES

[75] Inventors: Burkhard Köhler, Leverkusen; Klaus Horn, Dormagen; Helmut-Martin Meier, Ratingen, all of Germany

[73] Assignee: Bayer AG, Leverkusen, Germany

[21] Appl. No.: 603,087

[22] Filed: Feb. 20, 1996

[30] Foreign Application Priority Data

Mar. 3, 1995 [DE] Germany ................. 195 07 414.9
Apr. 4, 1995 [DE] Germany ................. 195 12 473.1

[51] Int. Cl.$^6$ ........................... C08K 5/54; C08K 5/20
[52] U.S. Cl. .................. 524/188; 524/157; 524/262; 524/265; 524/267
[58] Field of Search ........................ 523/213, 214; 524/157, 188, 262, 265, 267, 494

[56] References Cited

U.S. PATENT DOCUMENTS

| | | | |
|---|---|---|---|
| 4,306,073 | 12/1981 | Darms et al. | 556/419 |
| 4,578,409 | 3/1986 | Krishnan et al. | 524/394 |
| 4,638,027 | 1/1987 | Mark et al. | 524/157 |
| 4,783,494 | 11/1988 | Allen | 524/157 |
| 4,791,158 | 12/1988 | Lausberg et al. | 524/157 |
| 5,037,937 | 8/1991 | Komatsu et al. | 523/214 |
| 5,264,604 | 11/1993 | Neri et al. | 524/188 |
| 5,449,710 | 9/1995 | Umeda et al. | 524/265 |

FOREIGN PATENT DOCUMENTS

| | | |
|---|---|---|
| 0 188 767 | 7/1986 | European Pat. Off. . |
| 0 555 893 | 8/1993 | European Pat. Off. . |
| 42 24 769 | 2/1994 | Germany . |

*Primary Examiner*—Peter A. Szekely
*Attorney, Agent, or Firm*—Connolly and Hutz

[57] ABSTRACT

The present invention provides special silanes, their preparation and their use as plastics additives for improving the mechanical and flameproofing properties of the plastics.

3 Claims, No Drawings

SILANES CONTAINING OXALAMIDE FUNCTIONAL GROUPS AND THEIR USE AS PLASTICS ADDITIVES

Silanes containing a variety of functional groups are known and are described e.g. in no. 75 of Degussa's series of publications "Degussa Pigments-Silanes".

The known silanes, e.g. silanes containing amino functional groups, are not suitable for some applications since the amine nitrogen makes them too basic and too nucleophilic.

The object was therefore to prepare nitrogen-containing silanes of reduced nucleophilicity.

U.S. Pat. No. 4,578,409 describes halogen-containing phthalimides of aminosilanes. They are suitable as flameproofing additives, but the fact that they contain bromine or chlorine is undesirable for some applications. They do not affect the notch impact strength of polycarbonates.

In contrast, novel amides of oxalic acid with aminosilanes have been prepared which are technically easy to obtain. They improve the flame resistance of polycarbonates and the toughness of glass fibre-reinforced polycarbonates.

The invention therefore provides silanes containing oxalamide functional groups of formula (I):

$$(RO)_3Si-CH_2-CH_2-CH_2-NH-CO-CO-NH-CH_2-CH_2-CH_2-Si(OR)_3 \quad (I)$$

wherein

R is $C_1$–$C_{22}$-alkyl, $C_6$–$C_{12}$-aryl, $C_7$–$C_{12}$-aralkyl or radicals of formula (II):

$$R^1-O-CHR^2-CHR^3- \quad (II)$$

wherein $R^1$ is an ethyl or methyl radical and $R^2$ and $R^3$ independently of one another are hydrogen or methyl.

R is preferably methyl or ethyl.

The invention also provides a process for the preparation of the compounds of formula (I), which is characterized in that oxalic acid esters of formula (III):

$$RO-CO-CO-OR \quad (III)$$

wherein

R is as defined for formula (I), are mixed with 1.8 to 2.2 times the molar amount of silanes of formula (IV):

$$(RO)_3Si-CH_2-CH_2-CH_2-NH_2 \quad (IV)$$

wherein

R is again as defined for formula (I), the mixture is heated to temperatures of 65° C. to 200° C., preferably of 80° C. to 150° C., and the alcohols R—OH are distilled off.

The radicals R of the oxalic acid esters (III) are preferably identical to the radicals R of the silanes (IV) and are particularly preferably $CH_3$ or $C_2H_5$.

The reaction is preferably carried out without a solvent, or else is optionally carried out in the presence of inert solvents such as, for example, mesitylene, xylene or chlorobenzene. The pressure is between 0.001 bar and 5 bar, preferably between 0.9 bar and 1.1 bar. The reaction is preferably carried out without catalysts, or else is optionally carried out in the presence of catalysts such as, for example, organotin compounds like dibutyltin oxide, or strong bases like alkali metal alcoholates.

The silanes (I) according to the invention are obtained as a residue when the alcohols HOR are distilled off. They can be further purified by recrystallization or distillation under high vacuum.

The silanes (I) according to the invention are obtained as solids or oils.

They can be used as plastics additives for both thermoplastics and thermosets. Preferred thermoplastics are thermoplastic aromatic polycarbonates or thermoplastic polyamides; preferred thermosets are epoxy resins or unsaturated polyester resins (UP resins).

The silanes (I) according to the invention are particularly suitable as additives for glass fibre-reinforced plastics, i.e. for glass fibre-reinforced thermoplastics and for glass fibre-reinforced thermosets.

Thus the present invention also provides the use of the silanes (I) according to the invention as plastics additives.

The addition of the silanes (I) according to the invention improves the mechanical properties and the flame resistance of plastics, particularly of thermoplastics and very particularly of thermoplastic polycarbonates.

In terms of the present invention, thermoplastic aromatic polycarbonates are both homopolycarbonates and copolycarbonates; the polycarbonates can be linear or branched, in known manner.

These starting polycarbonates to be improved according to the invention are prepared in known manner from diphenols, carbonic acid derivatives, optionally chain terminators and optionally branching agents.

Details of the preparation of polycarbonates have been set out in many patent specifications for about 40 years. By way of example, only the following will be referred to here: Schnell, "Chemistry and Physics of Polycarbonates", Polymer Reviews, Volume 9, Interscience Publishers, New York, London, Sydney 1964; D. Freitag, U. Grigo, P. R. Müller, H. Nonvertue', BAYER AG, "Polycarbonates" in Encyclopedia of Polymer Science and Engineering, Volume 11, Second Edition, 1988, pages 648–718; and finally Dres. U. Grigo, K. Kirchner and P. R. Müller, "Polycarbonate" ("Polycarbonates") in Becker/Braun, Kunststoff-Handbuch (Plastics Handbook), Volume 3/1, Polycarbonate, Polyacetale, Polyester, Celluloseester (Polycarbonates, Polyacetals, Polyesters, Cellulose esters), Carl Hanser Verlag, Munich, Vienna 1992, pages 117–299.

Examples of diphenols suitable for the preparation of the polycarbonates to be improved according to the invention are hydroquinone, resorcinol, dihydroxybiphenyls, bis(hydroxyphenyl)alkanes, bis(hydroxyphenyl)cycloalkanes, bis(hydroxyphenyl) sulphides, bis(hydroxyphenyl) ethers, bis(hydroxyphenyl) ketones, bis(hydroxyphenyl) sulphones, bis(hydroxyphenyl) sulphoxides, α,α'-bis(hydroxyphenyl) diisopropylbenzenes and the ring-alkylated and ring-halogenated compounds thereof.

Preferred diphenols are 4,4'-dihydroxydiphenyl, 2,2-bis(4-hydroxyphenyl)propane, 2,4-bis(4-hydroxyphenyl)-2-methylbutane, 1,1-bis(4-hydroxyphenyl)-p-diisopropylbenzene, 2,2-bis(3-methyl-4-hydroxyphenyl) propane, 2,2-bis(3-chloro-4-hydroxyphenyl )propane, bis (3,5 -dimethyl -4-hydroxyphenyl )-methane, 2,2-bis(3,5-dimethyl-4-hydroxyphenyl )propane, bis(3,5-dimethyl-4-hydroxyphenyl)sulphone, 2,4-bis(3,5-dimethyl-4-hydroxyphenyl )-2-methylbutane, 1,1-bis(3,5-dimethyl-4-hydroxyphenyl)-p-diisopropylbenzene, 2,2-bis(3,5-dichloro-4-hydroxyphenyl)propane, 2,2-bis(3,5-dibromo-4-hydroxyphenyl)propane and 1,1-bis(4-hydroxyphenyl)-3,3,5-trimethylcyclohexane.

Particularly preferred diphenols are 2,2-bis(4-hydroxyphenyl)propane, 2,2-bis(3,5-dimethyl-4-hydroxyphenyl)

propane, 2,2-bis(3,5-dichloro-4-hydroxyphenyl)propane, 2,2-bis(3,5-dibromo-4-hydroxyphenyl)propane, 1,1-bis(4-hydroxy-phenyl)cyclohexane and 1,1-bis(4-hydroxyphenyl)-3,3,5-trimethylcyclohexane.

These and other suitable diphenols are described e.g. in U.S. Pat. No. 3,028,635, 2,999,835, 3,148,172, 2,991,273, 3,271,367, 4,982,014 and 2,999,846, German Offenlegungsschriften 1 570 703, 2 063 050, 2 036 052, 2 211 956 and 3 832 396, French patent 1 561 518, the monograph "H. Schnell, Chemistry and Physics of Polycarbonates, Interscience Publishers, New York 1964" and Japanese Offenlegungsschriften 62039/1986, 62040/1986 and 105550/1986.

In the case of the homopolycarbonates, only one diphenol is used; in the case of the copolycarbonates, several diphenols are used.

Examples of suitable carbonic acid derivatives are phosgene or diphenyl carbonate.

Suitable chain terminators are both monophenols and monocarboxylic acids. Suitable monophenols are phenol itself, alkylphenols such as cresols, p-tert-butylphenol, p-n-octylphenol, p-isooctylphenol, p-n-nonylphenol and p-isononylphenol, and halogenophenols such as p-chlorophenol, 2,4-dichlorophenol, p-bromophenol and 2,4,6-tribromophenol.

Suitable monocarboxylic acids are benzoic acid, alkylbenzoic acids and halogenobenzoic acids.

Preferred chain terminators are the phenols of formula (V):

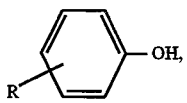

wherein

R is a branched or unbranched $C_8$- and/or $C_9$-alkyl radical.

The amount of chain terminator to be used is 0.1 mol % to 5 mol %, based on moles of the particular diphenols used. The chain terminators can be added before, during or after phosgenation.

Suitable branching agents are the trifunctional or more than trifunctional compounds known in polycarbonate chemistry, especially those with three or more than three phenolic OH groups.

Examples of suitable branching agents are phloroglucine, 4,6-dimethyl-2,4,6-tri(4-hydroxyphenyl)hept-2-ene, 4,6-dimethyl-2,4,6-tri(4-hydroxyphenyl)heptane, 1,3,5-tri(4-hydroxyphenyl)benzene, 1,1,1-tri(4-hydroxyphenyl)ethane, tri(4-hydroxyphenyl)phenylmethane, 2,2-bis[4,4-bis(4-hydroxyphenyl)cyclohexyl]propane, 2,4-bis(4-hydroxyphenylisopropyl)phenol, 2,6-bis(2-hydroxy-5'-methylbenzyl)-4-methylphenol, 2-(4-hydroxyphenyl)-2-(2, 4-dihydroxyphenyl)propane, hexa(4-(4-hydroxyphenyl isopropyl)phenyl) orthoterephthalate, tetra(4-hydroxyphenyl)methane, tetra(4-(4-hydroxyphenylisopropyl)phenoxy)methane and 1,4-bis(4', 4"-dihydroxytriphenyl)methyl)benzene, as well as 2,4-dihydroxybenzoic acid, trimesic acid, cyanuric chloride and 3,3-bis(3-methyl -4-hydroxyphenyl)-2-oxo-2,3-dihydroindole.

The amount of branching agents, if used, is 0.05 mol % to 2 mol %, again based on moles of the particular diphenols used.

The branching agents can either be placed in the aqueous-alkaline phase together with the diphenols and the chain terminators, or dissolved in an organic solvent and added before phosgenation. In the case of the transesterification process, the branching agents are used together with the diphenols.

All these measures for the preparation of the starting polycarbonates are familiar to the person skilled in the art.

In terms of the present invention, thermoplastic polyamides are polyamide 6, 66, 106, 11 and 12.

In terms of the present invention, epoxy resins are mixtures of diglycidyl ethers of bisphenols or polyglycidyl ethers of polyphenols with acid anhydrides or amines.

In terms of the present invention, unsaturated polyester resins (UP resins) are mixtures of polyesters of maleic acid or fumaric acid and diols with styrene.

The silanes (I) according to the invention are added to the plastics in amounts of 0.05 wt. % to 2 wt. %, preferably of 0.2 wt. % to 1.5 wt. %.

Thus the present invention also provides mixtures containing

A) 98 wt. % to 99.95 wt. %, preferably 99.8 wt. % to 98.5 wt. %, of plastics and B) 0.05 wt. % to 2 wt. %, preferably 0.2 wt. % to 1.5 wt. %, of silanes of formula (I), based in each case on 100 wt. % of A)+B).

The incorporation of the silanes (I) into the plastics differs somewhat according to the type of plastics.

The incorporation of the silanes (I) into thermoplastics, especially into thermoplastic polycarbonates or thermoplastic polyamides, is effected for example by mixing the silanes (I) with granules of the thermoplastics and then processing the mixture, or by metering a concentrate of the silanes (I) in the thermoplastics into said thermoplastics.

Thus the present invention also provides a process for the preparation of the mixtures according to the invention, containing thermoplastics and the silanes of formula (I), which is characterized in that the silanes (I), in amounts of 0.05 wt. % to 2 wt. %, preferably of 0.2 wt. % to 1.5 wt. %, based in each case on 100 wt. % of the total weight of thermoplastic and silane (I), are mixed, either as such or in the form of a concentrate of the silane (I) in said thermoplastics, with the thermoplastics in the melt at temperatures of 220° C. to 340° C., preferably of 250° C. to 300° C., in kneaders or extruders and the mixture is processed in known manner to granules or other shaped objects.

The incorporation of the silanes (I) into thermosets, especially into epoxy resins or unsaturated polyester resins, is effected for example by mixing with the uncured thermoset constituents and subsequent curing.

Thus the present invention also provides a process for the preparation of the mixtures according to the invention, containing thermosets and the silanes of formula (I) in amounts of 0.05 wt. % to 2 wt. %, preferably of 0.2 wt. % to 1.5 wt. %, based on 100 wt. % of the total weight of thermoset and silane (I), which is characterized in that the uncured components are mixed at temperatures of 20° to 100° C. and then cured at temperatures of 150° to 280° C.

In terms of the present invention, suitable glass fibres are any commercially available kinds and types of glass fibre, i.e. chopped strands with lengths of 3 to 6 mm, and milled fibres. The glass fibres used for preparing the moulding compounds are preferably made of E-glass. According to DIN 1259, E-glass is understood as meaning an aluminium borosilicate glass with an alkali metal oxide content of less than 1 wt. %. It is conventional to use glass fibres with diameters of 8 to 20 μm.

The glass fibres are added to the plastics to be improved, in known manner, in amounts of 5 wt. % to 70 wt. %, preferably of 10 wt. % to 40 wt. %, based on 100 wt. % of plastic and silane (I).

Thus the present invention also provides mixtures containing

A) 98 wt. % to 99.95 wt. %, preferably 98.5 wt. % to 99.8 wt %, of plastics,

B) 0.05 wt. % to 2 wt %, preferably 0.2 wt % to 1.5 wt. %, of silanes of formula (I), based in each case on 100 wt. % of A)+B), and additionally C) glass fibres in amounts of 5 wt. % to 70 wt. %, preferably of 10 wt % to 40 wt. %, based in each case on 100 wt. % of plastic and silane (I).

The present invention also provides a process for the preparation of the mixtures according to the invention, containing thermoplastics, the silanes of formula (I) and glass fibres, which is characterized in that the glass fibres, in amounts of 5 wt. % to 70 wt. %, preferably of 10 wt. % to 40 wt. %, based in each case on 100 wt. % of plastic and silane (I), are mixed, together with the silanes (I) or thereafter, with the thermoplastics in the melt at temperatures of 220° C. to 340° C., preferably of 250° C. to 300° C., in kneaders or extruders and the mixture is processed in known manner to granules or other shaped objects.

The present invention also provides a process for the preparation of the mixtures according to the invention, containing thermosets, the silanes of formula (I) and glass fibres, which is characterized in that the glass fibres, in amounts of 5 wt. % to 70 wt. %, preferably of 10 wt. % to 40 wt. %, based in each case on 100 wt. % of plastic and silane (I), are mixed, together with the silanes, with the uncured plastics at temperatures of 20° to 100° C. and the mixture is then cured.

The plastics according to the invention, containing the silanes (I), can optionally also contain other known additives, stabilizers, mould release agents, fillers, pigments etc. which are appropriate in each case for the individual plastics.

For thermoplastic polycarbonates, sulphonic acid salts may be mentioned in particular as additional flameproofing agents.

Suitable sulphonic acid salts are alkali metal salts, alkaline earth metal salts and ammonium salts, preferably the Li, Na and K salts of aromatic or aliphatic sulphonic acids, preferably of perfluorobutanesulphonic acid, perfluorooctanesulphonic acid, trichloromethylbenzene-sulphonic acid, diphenylbenzenesulphonic acid or formylbenzenesulphonic acid and the ketals or acetals thereof.

These sulphonic acid salts are added to the polycarbonates in the known amounts of up to 0.5 wt. %, based on 100 wt. % of polycarbonate, preferably of 0.001 wt. % to 0.5 wt. % and especially of 0.01 wt. % to 0.2 wt. %, again based on 100 wt. % of polycarbonate.

The incorporation of the sulphonic acid salts into the thermoplastic polycarbonates is known; in the present case, it can be carried out for example before the incorporation of the silanes (I) or together therewith.

Thus the present invention also provides mixtures containing

A) 98 wt. % to 99.95 wt. %, preferably 98.5 wt. % to 99.8 wt. %, of thermoplastic polycarbonates, B) 0.05 wt. % to 2 wt. %, preferably 0.2 wt. % to 1.5 wt. %, of silanes of formula (I), based in each case on 100 wt. % of A)+B), and additionally D) up to 0.5 wt. %, preferably from 0.001 wt. % to 0.5 wt. % and especially from 0.01 to 0.2 wt. %, of sulphonic acid salts, based in each case on 100 wt. % of thermoplastic polycarbonate.

The present invention also provides mixtures containing

A) 98 wt. % to 99.95 wt. %, preferably 98.5 wt. % to 99.8 wt. %, of thermoplastic polycarbonates, B) 0.05 wt. % to 2 wt. %, preferably 0.2 wt. % to 1.5 wt. %, of silanes of formula (I), based in each case on 100 wt. % of A)+B), additionally C) glass fibres in amounts of 5 wt. % to 70 wt. %, preferably 10 wt. % to 40 wt. %, based in each case on 100 wt. % of polycarbonate and silane (I), and additionally D) up to 0.5 wt. %, preferably from 0.001 wt. % to 0.5 wt. % and especially from 0.01 to 0.2 wt. %, of sulphonic acid salts, based in each case on 100 wt. % of thermoplastic polycarbonate.

The mixtures according to the invention can be made up either of freshly prepared polycarbonate resins or of scrap polycarbonate from shredded polycarbonate mouldings, it being possible for the glass fibres and/or the sulphonic acid salts to be already incorporated in the shredded polycarbonate mouldings.

The silanes (I) according to the invention are thus also suitable for the reprocessing of scrap polycarbonate, thereby assisting in the re-use of polycarbonate waste.

Thus the present invention also provides the use of the silanes of formula (I) for the reprocessing of polycarbonate waste.

The utilization of polycarbonate waste by means of siloxanes is known from DE-OS 4 224 769 (Le A 29 123), but in our opinion the use of the novel silanes of formula (I) according to the present invention cannot be derived therefrom.

The polycarbonate moulding compounds according to the invention can be processed on conventional processing machines by known methods to any desired shaped objects, including sheets.

The flame-resistant polycarbonate moulding compounds according to the invention are suitable for the manufacture of injection-moulded or extruded articles on which increased demands are made in terms of flame resistance, e.g. in the electrical, building, vehicle or aeronautics sector.

EXAMPLES

Preparation of the silanes (I)

Example 1

275 g of aminopropyltriethoxysilane are mixed with 92 g of diethyl oxalate, the mixture warming up to ca. 80° C. The ethanol is then distilled off under normal pressure at a bath temperature of 120° C.

Example 2

358 g of aminopropyltrimethoxysilane are mixed with 118 g of dimethyl oxalate, the mixture warming up to ca. 70° C. The methanol is then distilled off under normal pressure at a bath temperature of 110° C.

Use of the silanes (I)

Example 3

A bisphenol A polycarbonate with a viscosity $\eta_{rel}$ of 1.305 was melted in a double-shaft extruder at temperatures of 300° to 320° C. A mixture of 10 wt. % of chopped strands, 0.5 wt. % of mould release agent, 0.15 wt. % of potassium perfluorobutanesulphonate and 0.25 wt. % of additive according to Example 1 was then metered directly into the polycarbonate melt.

The polymer strand was cooled and granulated.

The granules were dried (vacuum drying cabinet) and then injection-moulded to test pieces of dimensions 127×

12.7×1.6 mm on an injection-moulding machine at a bulk temperature of 280° C.

The test bars were then subjected to a flammability test in accordance with UL 94 (flammability of solid samples of plastics, Underwriters Laboratories) and assigned to flammability class V0.

Example 4

A bisphenol A polycarbonate with a viscosity $\eta_{rel}$ of 1.305 was melted in a double-shaft extruder at temperatures of 300° to 320° C. A mixture of 10 wt. % of chopped strands, 0.5 wt. % of mould release agent, 0.15 wt. % of potassium perfluorobutanesulphonate and 0.50 wt. % of additive according to Example 1 was then metered directly into the polycarbonate melt.

The polymer strand was cooled and granulated.

The granules were dried (vacuum drying cabinet) and then injection-moulded to test pieces of dimensions 127× 12.7×1.6 mm on an injection-moulding machine at a bulk temperature of 280° C.

The test bars were then subjected to a flammability test in accordance with UL 94 (flammability of solid samples of plastics, Underwriters Laboratories) and assigned to flammability class V0.

Example 5

5 kg of moulded objects consisting of polycarbonate reinforced with 10 wt. % of glass fibres (but not including flameproofing salts and/or halogen-containing phthalimides) were shredded and 0.15 wt. % of potassium perfluorobutanesulphonate and 0.5 wt. % of additive according to Example 1 were then added to the shredded material.

The mixture was then injection-moulded to test pieces of dimensions 127×12.7×1.6 mm on an injection-moulding machine at a bulk temperature of 280° C.

The test bars were then subjected to a flammability test in accordance with UL 94 (flammability of solid samples of plastics, Underwriters Laboratories). The material was assigned to flammability class V0.

Comparative Example 1

The procedure was as in Example 3 but without the addition of 0.25 wt. % of additive according to Example 1. The material was assigned to flammability class V2.

Comparative Example 2

The procedure was as in Example 3 but without the addition of 0.15 wt. % of potassium perfluorobutanesulphonate and 0.25 wt. % of additive according to Example 1. The material was assigned to flammability class V2.

Comparative Example 3

The procedure was as in Example 4 but without the addition of 0.50 wt. % of additive according to Example 1. The material was assigned to flammability class V2.

Comparative Example 4

The procedure was as in Example 4 but without the addition of 0.15 wt. % of potassium perfluorobutanesulphonate and 0.50 wt. % of additive according to Example 1. The material was assigned to flammability class V2.

Example 6

5 kg of moulded objects consisting of polycarbonate reinforced with 10 wt. % of glass fibres and flameproofed with 0.15 wt. % of potassium perfluorobutanesulphonate (but not including halogen-containing phthalimides) were shredded and 0.5 wt. % of additive according to Example 1 was then added to the shredded material.

The mixture was then injection-moulded to test pieces of dimensions 127×12.7×1.6 mm on an injection-moulding machine at a bulk temperature of 280° C.

The test bars were then subjected to a flammability test in accordance with UL 94 (flammability of solid samples of plastics, Underwriters Laboratories). The material was assigned to flammability class V0.

Comparative Example 5

The procedure was as in Example 6 but without the addition of 0.5 wt. % of additive according to Example 1. The material was assigned to flammability class V2.

Example 7

5 kg of shaped objects consisting of the compound of Example 4 were shredded. 20 wt. % of this shredded material was intermixed with the compound of Example 6. The mixture was then injection-moulded to test pieces of dimensions 127×12.7×1.6 mm on an injection-moulding machine at a bulk temperature of 280° C.

The test bars were then subjected to a flammability test in accordance with UL 94 (flammability of solid samples of plastics, Underwriters Laboratories). The material was assigned to flammability class V0 for a thickness of 1.6 mm.

Example 8

A bisphenol A polycarbonate with a viscosity $\eta_{rel}$ of 1.305 was melted in a double-shaft extruder at temperatures of 300° to 320° C. A mixture of 0.5 wt. % of mould release agent, 0.15 wt. % of potassium perfluorobutanesulphonate and 0.50 wt. % of additive according to Example 1 was then metered directly into the polycarbonate melt.

The polymer strand was cooled and granulated.

The granules were dried (vacuum drying cabinet) and then injection-moulded to test pieces of dimensions 127× 12.7×1.6 mm on an injection-moulding machine at a bulk temperature of 280° C.

The test bars were then subjected to a flammability test in accordance with UL 94 (flammability of solid samples of plastics, Underwriters Laboratories). The material was assigned to flammability class V0.

Comparative Example 6

The procedure was as in Example 8 except that no additive according to Example 1 was added to the mixture. The test bars were then subjected to a flammability test in accordance with UL 94 (flammability of solid samples of plastics, Underwriters Laboratories). The material was assigned to flammability class V2.

Example 9

A bisphenol A polycarbonate with a viscosity $\eta_{rel}$ of 1.305 was melted in a double-shaft extruder at temperatures of 300° to 320° C. A mixture of 30 wt. % of milled fibre and 0.075 wt. % of additive according to Example 1 was then metered directly into the polycarbonate melt.

The polymer strand was cooled and granulated.

The granules were dried (vacuum drying cabinet) and then injection-moulded to test pieces of dimensions 50×6×4 mm on an injection-moulding machine at a bulk temperature of 280° C.

The test pieces were then subjected to a Charpy impact strength test in accordance with DIN 53453. The measured impact strength was 33 kJ/m².

Comparative Example 7

The procedure was as in Example 9 except that no additive according to Example 1 was added to the mixture. The test bars were then subjected to a Charpy impact strength test in accordance with DIN 53453. The measured impact strength was 21 kJ/m².

We claim:

1. Mixtures consisting of
   A) 98 wt % to 99.95 wt % of thermoplastic polycarbonates derived from 2,2-bis-(4-hydroxyphenyl)-propane and/or from 1,1-bis(4-hydroxyphenyl)-3,3,5-trimethylcyclohexane and from phenol or alkylphenols,
   B) 0.05 wt. % to 2 wt. % of silanes of formula (I)

$$(RO)_3Si-CH_2-CH_2-CH_2-NH-CO-CO-NH-CH_2-CH_2-CH_2-Si(OR)_3 \quad (I)$$

wherein
   R is $C_2$–$C_{22}$-alkyl, $C_6$–$C_{12}$-aryl, $C_7$–$C_{12}$-aralkyl or radicals of formula (II):

$$R^1-O-CHR^2-CHR^3- \quad (II)$$

wherein
   $R^1$ is an ethyl or methyl radical and
   $R^2$ and $R^3$ independently of one another are hydrogen or methyl,
   based in each case on 100 wt % of A) and B), and
   C) glass fibers in amounts of 10 wt % to 40 wt %, based on wt % of thermoplastic polycarbonates and silanes (I).

2. Mixtures consisting of
   A) 98 wt % to 99.95 wt % of thermoplastic polycarbonates derived from 2,2-bis-(4-hydroxyphenyl)-propane and/or from 1,1-bis(4-hydroxyphenyl)-3,3,5-trimethylcyclohexane and from phenol or alkylphenols,
   B) 0.05 wt % to 2 wt % of silanes of formula (I)

$$(RO)_3Si-CH_2-CH_2-CH_2-NH-CO-CO-NH-CH_2-CH_2-CH_2-Si(OR)_3 \quad (I)$$

wherein
   R is $C_1$–$C_{22}$-alkyl, $C_6$–$C_{12}$-aryl, $C_7$–$C_{12}$-aralkyl or radicals of formula (II):

$$R^1-O-CHR^2-CHR^3- \quad (II)$$

wherein
   $R^1$ is an ethyl or methyl radical and
   $R^2$ and $R^3$ independently of one another are hydrogen or methyl, based in each case on 100 wt % of A) and B), and
   C) 0.01 wt % to 0.2 wt % of sulphonic acid salts, based on 100 wt % of thermoplastic polycarbonate.

3. Mixtures consisting of
   A) 98 wt % to 99.95 wt % of thermoplastic polycarbonates derived from 2,2-bis-(4-hydroxyphenyl)-propane and/or from 1,1-bis-(4-hydroxyphenyl)-3,3,5-trimethylcyclohexane and from phenol or alkylphenols,
   B) 0.05 wt % to 2 wt % of silanes of formula (I)

$$(RO)_3Si-CH_2-CH_2-CH_2-NH-CO-CO-NH-CH_2-CH_2-CH_2-Si(OR)_3 \quad (I)$$

wherein
   R is $C_1$–$C_{22}$-alkyl, $C_6$–$C_{12}$-aryl, $C_7$–$C_{12}$-aralkyl or radicals of formula (II):

$$R^1-O-CHR^2-CHR^3- \quad (II)$$

wherein
   $R^1$ is an ethyl or methyl radical and
   $R^2$ and $R^3$ independently of one another are hydrogen or methyl,
   based in each case on 100 wt % of A) and B),
   C) glass fibers in amounts of 10 wt % to 40 wt %, based on 100 wt % of thermoplastic polycarbonates and silanes (I), and
   D) 0.01 wt % to 0.2 wt % of sulphonic acid salts, based on 100 wt % of thermoplastic polycarbonate.

* * * * *